(12) United States Patent
Sudol et al.

(10) Patent No.: US 11,426,140 B2
(45) Date of Patent: Aug. 30, 2022

(54) INTRA-CARDIAC ECHOCARDIOGRAPHY INTERPOSER

(71) Applicant: KONINKLIJKE PHILIPS N.V., Eindhoven (NL)

(72) Inventors: Wojtek Sudol, Andover, MA (US); William John Ossmann, Acton, MA (US); Stephen Davies, El Dorado Hills, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 701 days.

(21) Appl. No.: 16/338,820

(22) PCT Filed: Oct. 3, 2017

(86) PCT No.: PCT/EP2017/075092
§ 371 (c)(1),
(2) Date: Apr. 2, 2019

(87) PCT Pub. No.: WO2018/065425
PCT Pub. Date: Apr. 12, 2018

(65) Prior Publication Data
US 2019/0282204 A1    Sep. 19, 2019

Related U.S. Application Data

(60) Provisional application No. 62/434,489, filed on Dec. 15, 2016, provisional application No. 62/403,278, filed on Oct. 3, 2016.

(51) Int. Cl.
*A61B 8/12* (2006.01)
*A61B 8/08* (2006.01)
(Continued)

(52) U.S. Cl.
CPC .............. *A61B 8/12* (2013.01); *A61B 8/0883* (2013.01); *A61B 8/0891* (2013.01); *A61B 8/4444* (2013.01); *A61B 8/4483* (2013.01); *A61B 8/4494* (2013.01); *B06B 1/0215* (2013.01); *B06B 1/0292* (2013.01); *B06B 1/067* (2013.01);
(Continued)

(58) Field of Classification Search
None
See application file for complete search history.

(56) References Cited

U.S. PATENT DOCUMENTS

2009/0306518 A1    12/2009   Kurse et al.
2012/0238880 A1     9/2012   Davidsen
(Continued)

FOREIGN PATENT DOCUMENTS

WO    2016113638 A1    7/2016

*Primary Examiner* — Yi-Shan Yang (57) ABSTRACT

An imaging catheter assembly is provided. The imaging catheter assembly includes an interposer including a multi-layered substrate structure, wherein the multi-layered substrate structure includes a first plurality of conductive contact pads coupled to a second plurality of conductive contact pads via a plurality of conductive lines; an imaging component coupled to the interposer via the first plurality of conductive contact pads; and an electrical cable coupled to the interposer via the second plurality of conductive contact pads and in communication with the imaging component.

26 Claims, 11 Drawing Sheets

(51) Int. Cl.
  *A61B 8/00* (2006.01)
  *B06B 1/02* (2006.01)
  *B06B 1/06* (2006.01)
  *H01L 23/00* (2006.01)
  *H01L 25/16* (2006.01)

(52) U.S. Cl.
  CPC ............ *B06B 1/0622* (2013.01); *H01L 24/48* (2013.01); *H01L 25/162* (2013.01); *B06B 2201/76* (2013.01); *H01L 2224/48157* (2013.01)

(56) References Cited

U.S. PATENT DOCUMENTS

| | | | |
|---|---|---|---|
| 2013/0251467 A1 | 9/2013 | Stemmer | |
| 2013/0261467 A1* | 10/2013 | Dausch | A61B 8/12 600/466 |
| 2013/0303919 A1 | 11/2013 | Corl | |
| 2015/0115773 A1* | 4/2015 | Li | A61B 8/12 310/335 |
| 2016/0374710 A1* | 12/2016 | Sinelnikov | A61B 8/481 600/439 |
| 2018/0264519 A1* | 9/2018 | Sudol | A61B 8/12 |

* cited by examiner

INTRA-CARDIAC ECHOCARDIOGRAPHY INTERPOSER

RELATED APPLICATIONS

This application is the U.S. National Phase application under 35 U.S.C. § 371 of International Application No. PCT/EP2017/075092, filed on Oct. 3, 2017, which claims the benefit of and priority to U.S. Provisional Application No. 62/403,278, filed Oct. 3, 2016, and 62/434,489, filed Dec. 15, 2016, which are incorporated by reference in their entireties.

TECHNICAL FIELD

The present disclosure relates generally to imaging catheters, in particular, to imaging assemblies and the interconnection between an imaging assembly and a cable of an imaging system.

BACKGROUND

Diagnostic and therapeutic ultrasound catheters have been designed for use inside many areas of the human body. In the cardiovascular system, two common diagnostic ultrasound methods are intravascular ultrasound (IVUS) and intra-cardiac echocardiography (ICE). Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

IVUS catheters are typically used in the large and small blood vessels (arteries or veins) of the body, and are almost always delivered over a guidewire having a flexible tip. ICE catheters are usually used to image chambers of the heart and surrounding structures, for example, to guide and facilitate medical procedures, such as transseptal lumen punctures, left atrial appendage closures, atrial fibrillation ablation, and valve repairs. Commercially-available ICE catheters are not designed to be delivered over a guidewire, but instead have distal ends which can be articulated by a steering mechanism located in a handle at the proximal end of the catheter. For example, an ICE catheter may be inserted through the femoral or jugular vein when accessing the anatomy, and steered in the heart to acquire images necessary to the safety of the medical procedures.

An ICE catheter typically includes an ultrasound imaging component that generates and receives acoustic energy. The imaging component may include an array of transducer elements or transducer elements arranged in any suitable configuration. The imaging component is encased in a tip assembly located at a furthest distal tip of the catheter. The tip assembly is covered with acoustic adhesive materials. An electrical cable is connected to the imaging component and extends through the core of the body of the catheter. The electrical cable may carry control signals and echo signals to facilitate imaging of the heart anatomy. The device may provide rotational, 2-way, or 4-way steering mechanisms such that anterior, posterior, left, and/or right views of the heart anatomy may be imaged.

One approach to interconnecting an electrical cable to an imaging component of an imaging catheter is to directly connect or solder the electrical cable to the imaging component. However, the direct interconnection may create tension on the imaging component while the catheter is maneuvered to a desired location, and thus may not be desirable. Another approach is to employ a separate flex circuit or printed circuit board (PCB) to interconnect the electrical cable and the imaging component. For example, components, such as capacitors and thermistors, may be mounted on the PCB to provide the interconnection. The PCB may include traces or signal lines and vias. The traces may have widths of about 20 micrometers (µm) to about 50 µm and may be spaced apart by about 20 µm to about 50 µm. The vias may have sizes in the range of hundreds of µm. Thus, although the use of a separate flex circuit or PCB may reduce tension on the imaging component, the flex circuit or the PCB may not be suitable for use in an imaging catheter due to the limited space available within the imaging catheter.

SUMMARY

The invention provides devices, systems, and related methods for interconnecting imaging assemblies with electrical cables of imaging systems that overcome the limitations associated with previous designs.

Embodiments of the present disclosure provide an interposer device suitable for interconnecting an imaging component and an electrical cable. The interposer device is formed from a multi-layered substrate structure including at least one intermediate conductive metal layer positioned between a top metal layer and a base substrate layer. The top metal layer is plated with electroless nickel palladium immersion gold (ENEPIG) to from conductive contact pads. The ENEPIG material is suitable for both soldering and wirebonding. The intermediate conductive metal layer is patterned with conductive traces to form signal paths between the conductive contact pads. In an embodiment, the imaging component is wire-bonded to the interposer via a first subset of the conductive contact pads. The electrical cable is soldered to the interposer via a second subset of the conductive contact pads. Additional surface-mount components can be mounted on a third subset of the conductive contact pads to provide additional functionalities such as power regulation. The interposer device provide dense and precise signal traces for signal distribution and routing without including any logic as in typical semiconductor devices. The dense and precise placement of the signal traces allows the interposer device to have a form factor suitable for use in catheter assembly.

In one embodiment, an imaging catheter assembly is provided. The imaging catheter includes an interposer including a multi-layered substrate structure, wherein the multi-layered substrate structure includes a first plurality of conductive contact pads coupled to a second plurality of conductive contact pads via a plurality of conductive lines; an imaging component coupled to the interposer via the first plurality of conductive contact pads; and an electrical cable coupled to the interposer via the second plurality of conductive contact pads and in communication with the imaging component.

In some embodiments, the interposer includes: a top conductive layer including the first plurality of conductive contact pads and the second plurality of conductive contact pads; a base substrate material layer; and at least one intermediate conductive layer positioned between the top conductive layer and the base substrate material layer, wherein the plurality of conductive lines extend through the at least one intermediate conductive layer. In some embodiments, the base substrate material layer includes at least one of ceramic, glass, quartz, alumina, sapphire, or silicon. In some embodiments, the top conductive layer further includes: a third plurality of conductive contact pads coupled to the plurality of conductive lines; and a surface-mount component mounted on the third plurality of conductive contact pads. In some embodiments, the surface-mount component is a power-regulating component. In some embodiments, the interposer has a width less than 4 millimeter (mm). In some embodiments, the interposer has a length less than 15 millimeter (mm). In some embodiments, the imaging component is wire-bonded to the interposer via the first plurality of conductive contact pads. In some embodiments, the electrical cable is soldered to the interposer via the second plurality of conductive contact pads. In some embodiments, the imaging component includes an integrated circuit (IC) layer positioned between an acoustic layer and a backing layer. In some embodiments, the imaging component is a planar component, and wherein the interposer is positioned coplanar or parallel to a plane of the imaging component. In some embodiments, the backing layer is longer than the IC layer such that a portion of the backing layer extends beyond the IC layer, and wherein the interposer is positioned on the portion of the backing layer that extends beyond the IC layer. In some embodiments, the plurality of conductive lines includes at least one of a power line, a control line, or a signal line. In some embodiments, the imaging catheter assembly further comprises a flexible elongate member including a distal portion and a proximal portion, wherein the imaging component and the interposer are coupled to the distal portion of the flexible elongate member.

In one embodiment, a method of manufacturing an imaging catheter assembly is provided. The method includes forming an interposer comprising a multi-layered substrate structure including a first plurality of conductive contact pads coupled to a second plurality of conductive contact pads via a plurality of conductive lines; coupling an imaging component to the first plurality of conductive contact pads of the interposer; and coupling an electrical cable to the second plurality of conductive contact pads of the interposer.

In some embodiments, the forming the interposer includes: forming a base substrate material layer; forming a top conductive layer including the first plurality of conductive contact pads and the second plurality of conductive contact pads; and forming one or more intermediate conductive layers positioned between the top conductive layer and the base substrate material layer, wherein the plurality of conductive lines extend through the one or more intermediate conductive layers. In some embodiments, the method further comprises coupling a surface-mount component to interposer. In some embodiments, the coupling the electrical cable to the second plurality of conductive contact pads includes soldering. In some embodiments, the coupling the imaging component to the first plurality of conductive contact pads includes wirebonding. In some embodiments, the method further comprises mounting the interposer to a backing layer of the imaging component.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the intraluminal system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
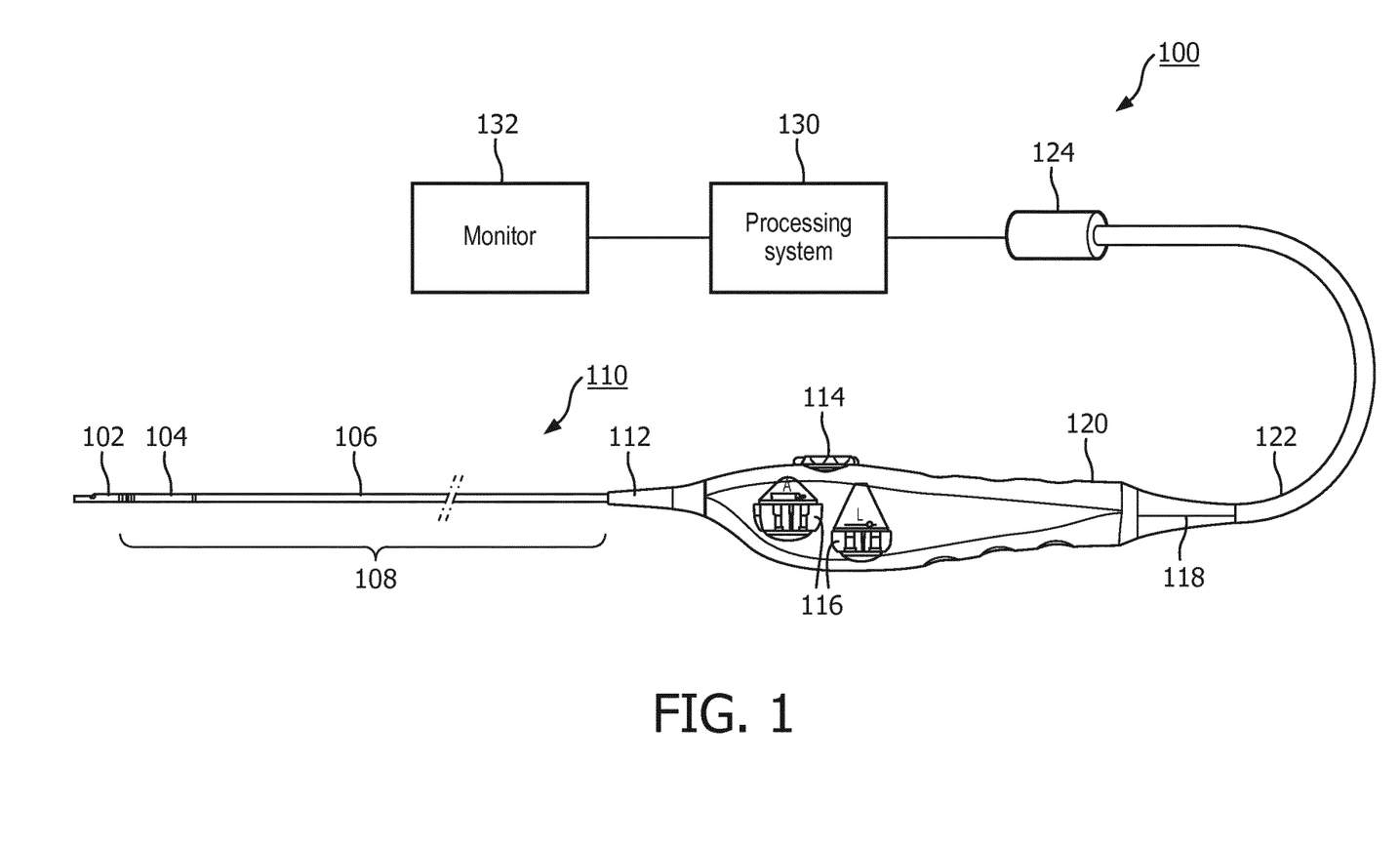
FIG. 1 is a schematic diagram of an intraluminal imaging system according to embodiments of the present disclosure.

FIG. 1 is a schematic diagram of an intraluminal imaging system 100 according to embodiments of the present disclosure. The system 100 may include an intraluminal device 110, a connector 124, a control and processing system 130, such as a console and/or a computer, and a monitor 132. The intraluminal device 110 includes a tip assembly 102, a flexible elongate member 108, and a handle 120. The flexible elongate member 108 includes a distal portion 104 and a proximal portion 106. The distal end of the distal portion 104 is attached to the tip assembly 102. The proximal end of the proximal portion 106 is attached to the handle 120 for example, by a resilient strain reliever 112, for manipulation of the intraluminal device 110 and manual control of the intraluminal device 110. The tip assembly 102 can include an imaging component with ultrasound transducer elements and associated circuitry. The handle 120 can include actuators 116, a clutch 114, and other steering control components for steering the intraluminal device 110. In an embodiment, the intraluminal device 110 is an ICE device.

The handle 120 is connected to the connector 124 via another strain reliever 118 and an electrical cable 122. The connector 124 may be configured in any suitable configurations to interconnect with the processing system 130 and the monitor 132 for processing, storing, analyzing, manipulating, and displaying data obtained from signals generated by the imaging component at the tip assembly 102. The processing system 130 can include one or more processors, memory, one or more input devices, such as keyboards and any suitable command control interface device. The processing system 130 can be operable to facilitate the features of the intraluminal imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician advances the flexible elongate member 108 into a vessel within a heart anatomy. The physician or clinician can steer the flexible elongate member 108 to a position near the area of interest to be imaged by controlling the actuators 116 and the clutch 114 on the handle 120. For example, one actuator 116 may deflect the tip assembly 102 and the distal portion 104 in a left-right plane and the other actuator 116 may deflect the tip assembly 102 and the distal portion 104 in an anterior-posterior plane. The clutch 114 provides a locking mechanism to lock the positions of the actuators 116 and in turn the deflection of the flexible elongate member 108 while imaging the area of interest.

The imaging process may include activating the ultrasound transducer elements on the tip assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the processing system 130 where the ultrasound image is reconstructed and displayed on the monitor 132. In some embodiments, the processing system 130 can control the activation of the ultrasound transducer elements and the reception of the echo signals. In some embodiments, the processing system 130 and the monitor 132 may be part of the same system.

The system 100 may be utilized in a variety of applications such as transseptal punctures, left atrial appendage closures, atrial fibrillation ablation, and valve repairs and can be used to image vessels and structures within a living body. In addition, the tip assembly 102 may include any suitable physiological sensor or component for diagnostic, treatment, and/or therapy. For example, the tip assembly can include an imaging component, an ablation component, a cutting component, a morcellation component, a pressure-sensing component, a flow-sensing component, a temperature-sensing component, and/or combinations thereof.

Figure 2:
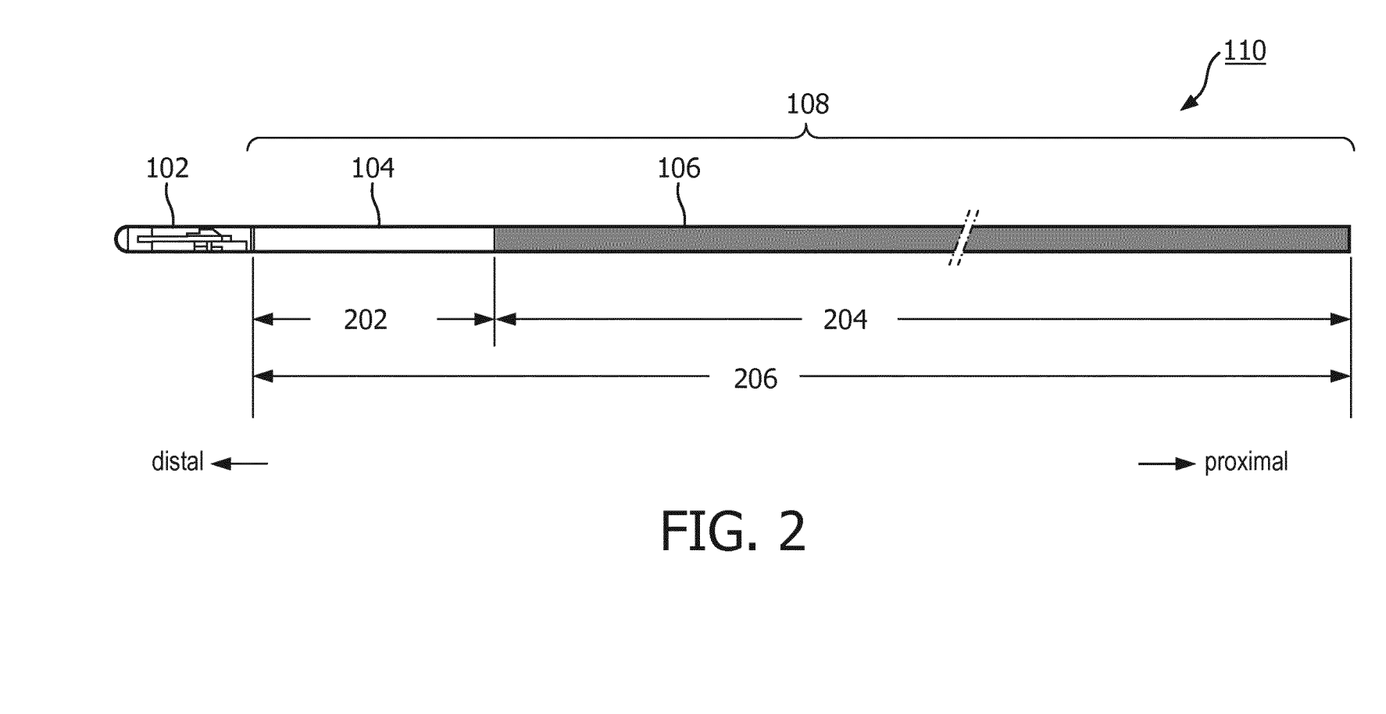
FIG. 2 is a schematic diagram of a portion of an intraluminal device according to embodiments of the present disclosure.

FIG. 2 is a schematic diagram of a portion of the intraluminal device 110 according to embodiments of the present disclosure. The tip assembly 102 and the flexible elongate member 108 are shaped and sized for insertion into vessels of a patient body. The flexible elongate member 108 can be composed of any suitable material, such as Pebax® polyether block amides. The distal portion 104 and the proximal portion 106 are tubular in shape and may include one or more lumens extending along a length of the flexible elongate member 108. In some embodiments, one lumen (e.g., a primary lumen) may be sized and shaped to accommodate an electrical cable 340 (shown in FIG. 3) interconnecting the tip assembly 102 and the connector 124 for transferring echo signals obtained from the transducer elements. In addition, the lumen may be shaped and sized to accommodate other components for diagnostic and/or therapy procedures. In some other embodiments, one or more lumens (e.g., secondary lumens) may be sized and shaped to accommodate steering wires, for example, extending from the distal portion 104 to the handle 120. The steering wires may be coupled to the actuators 116 and the clutch 114 such that the flexible elongate member 108 and the tip assembly 102 are deflectable based on actuations of the actuators 116 and the clutch 114. Dimensions of the flexible elongate member 108 can vary in different embodiments. In some embodiments, the flexible elongate member 108 can be a catheter having an outer diameter between about 8 and about 12 French (Fr) and can have a total length 206 between about 80 centimeters (cm) to about 120 cm, where the proximal portion 106 can have a length 204 between about 70 cm to about 118 cm and the distal portion 104 can have a length 202 between about 2 cm to about 10 cm.

Figure 3:
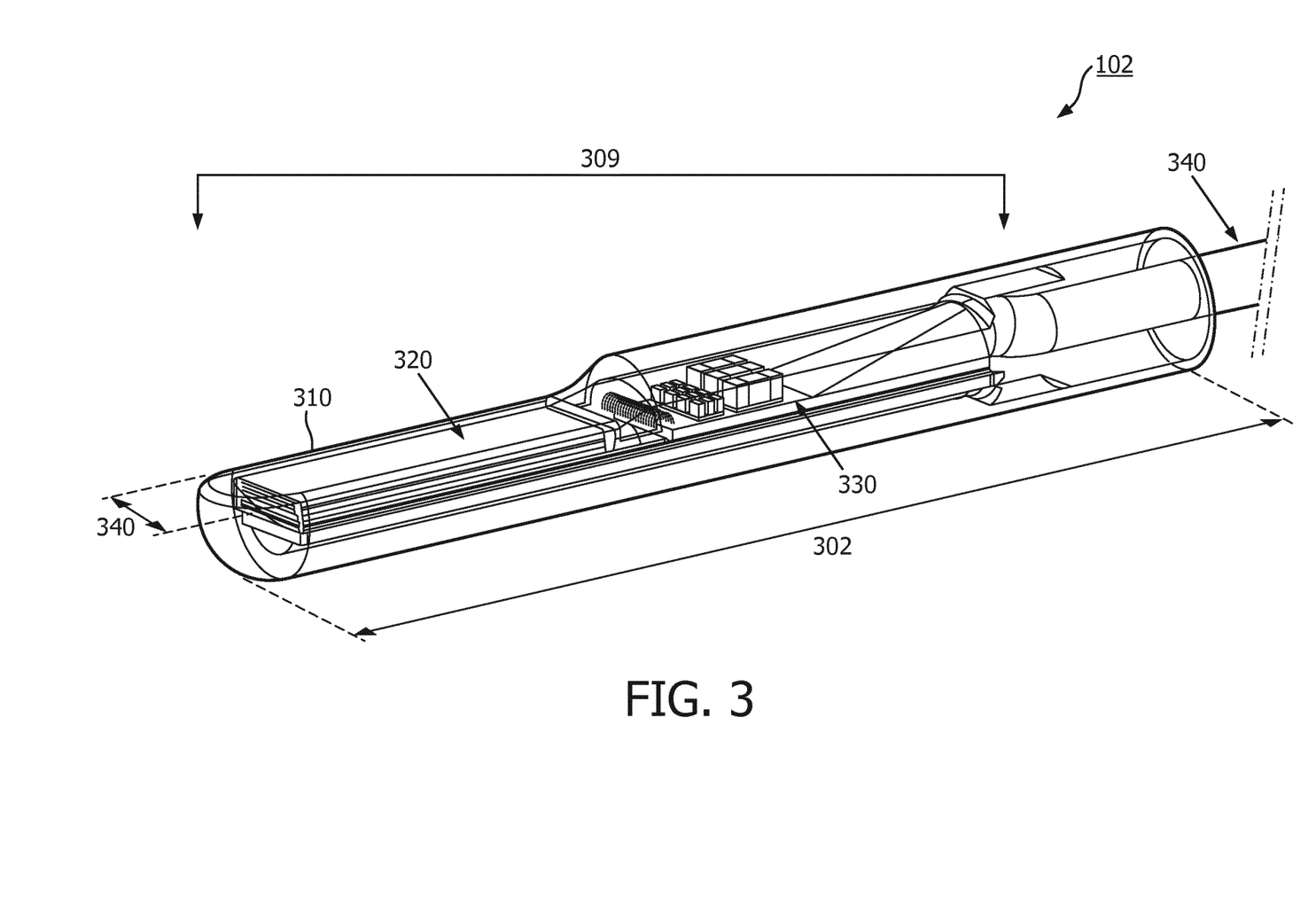
FIG. 3 is a schematic diagram of a tip assembly according to embodiments of the present disclosure.

FIG. 3 is a schematic diagram of the tip assembly 102 according to embodiments of the present disclosure. FIG. 3 provides a more detailed view of the tip assembly 102. The tip assembly 102 includes a tip member 310, an imaging component 320, and an interposer 330. The tip member 310 has a tubular body sized and shaped for insertion into a patient body. The tip member 310 can be composed of a thermoplastic elastomer material or any suitable biocompatible material that has acoustic impedance matching to blood within a vessel of a patient body when in use. For example, the tip member 310 can be composed of Pebax® polyether block amides. Dimensions of the tip member 310 can vary in different embodiments and may depend on the size of the catheter or the flexible elongate member 108. In some embodiments, the tip member 310 can include a length 302 between about 15 millimeter (mm) to about 30 mm and a width 304 between about 2 mm to about 4 mm.

The interposer 330 interconnects the imaging component 320 to an electrical cable 340. The imaging component 320 emits ultrasound energy and receives ultrasound echo signals reflected by surrounding tissues and vasculatures. The imaging component 320 is described in greater detail herein with references to FIG. 4. The electrical cable 340 carries the ultrasound echo signals to the processing system 130 for image generation and analysis. In addition, the electrical cable 340 can carry control signals for controlling the imaging component 320. Further, the electrical cable 340 can carry power for powering the imaging component 320. The electrical cable 340 extends along a length of the flexible elongate member 108. The interposer 330 functions as an interconnect to distribute or transfer signals between the imaging component 320 and the electrical cable 340. The interposer 330 can be composed of any suitable substrate material, such as ceramic, glass, quartz, alumina, sapphire, and silicon, that may provide high-density signal routing in a small form factor. In some embodiments, the interposer 330 may leverage semiconductor processes, but may not include active components such as transistors as in typical semiconductor devices. The interposer 330 is described in greater detail herein with references to FIGS. 5-10.

Figures 4A, 4B:
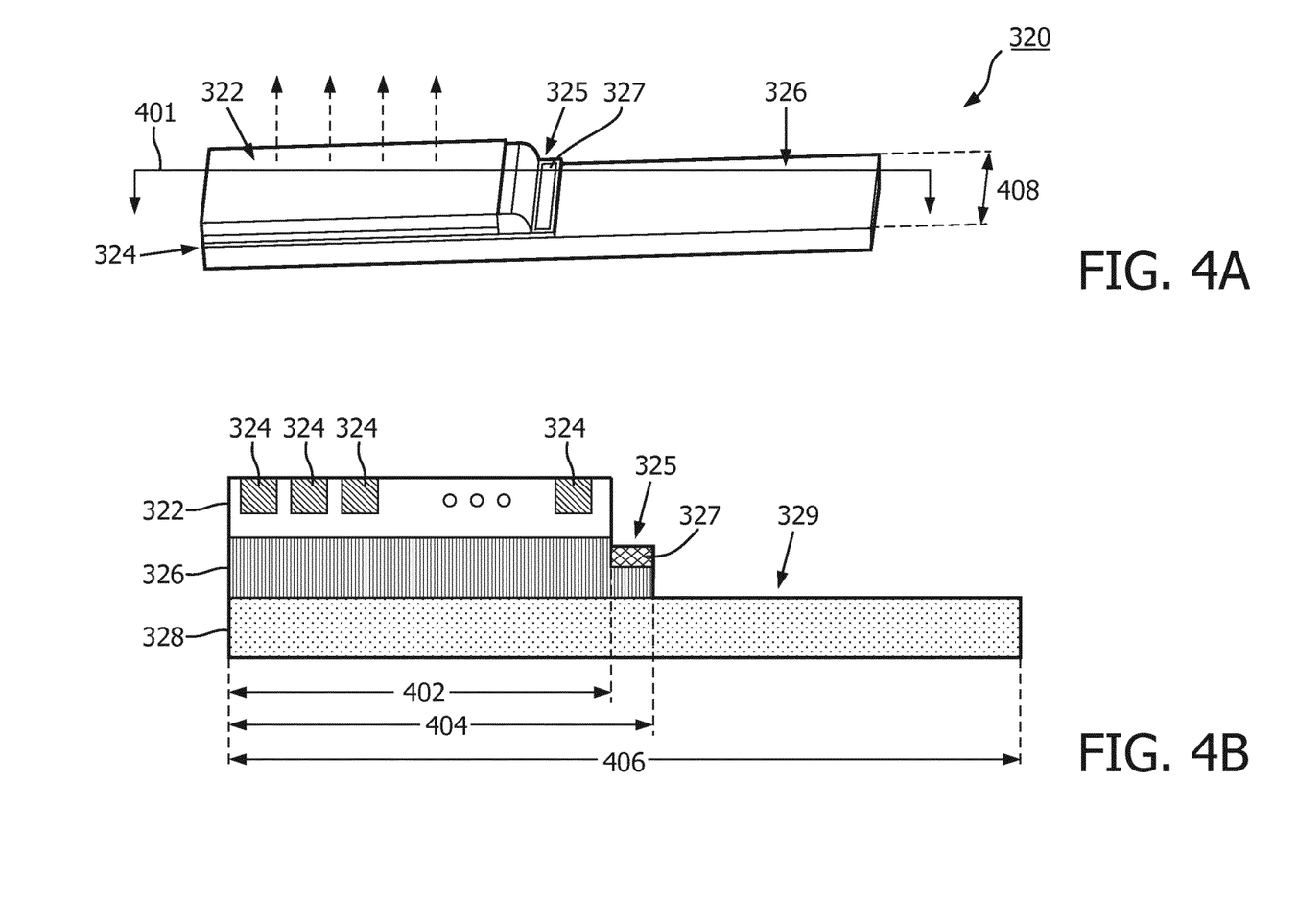
FIG. 4A is a perspective view of an imaging component according to embodiments of the present disclosure.
FIG. 4B is a cross-sectional view of an imaging component according to embodiments of the present disclosure.

FIG. 4A is a perspective view of the imaging component 320 according to embodiments of the present disclosure. FIG. 4B is a cross-sectional view of the imaging component 320 take along the line 401 of FIG. 4A according to embodiments of the present disclosure. The imaging component 320 is a planar component including an acoustic layer 322, an integrated circuit (IC) layer 326, and a backing layer 328. The IC layer 326 is positioned between the acoustic layer 322 and the backing layer 328. In some other embodiments, the backing layer 328 may be between the acoustic layer 322 and the IC layer 326 with electrical connections made through the backing layer 328.

The acoustic layer 322 includes an array of ultrasound transducer elements 324. The ultrasound transducer elements 324 are composed of piezoelectric material and acoustic matching layers. In alternative embodiments, the ultrasound transducer elements 324 may be capacitive micromachined ultrasound transducers (cMUTs). Exemplary transducers for ICE have a typical thickness of approximately 0.28 mm in the piezoelectric material to enable an 8 megahertz (MHz) ultrasound signal to be generated and transmitted at a typical velocity of 1500 meter per second (m/sec) through blood. The ultrasound signal may propagate in the direction as shown by the dashed arrows. The transducer thickness can be of various thicknesses ranging approximately from 0.56 mm to 0.19 mm to generate sufficient penetration depth in tissue imaging. In general, the thickness of the transducers can be adjusted for the frequency of sound in the transmission medium for the desired penetration depth in any tissue imaging. Image intensity can be adjusted by the driving voltage on the transducers. In some embodiments, the acoustic layer 322 may include a linear array of about 32 to about 128 ultrasound transducer elements 324 for two-dimensional (2D) imaging. In some other embodiments, the acoustic layer 322 may include a matrix of about 200 to about 2000 ultrasound transducer elements 324 for three-dimensional (3D) imaging.

The IC layer 326 includes logics and/or circuits configured to multiplex control signals, for example, generated by the processing system 130, and transfer the control signals to corresponding ultrasound transducer elements 324. The controls signals can control the emission of ultrasound pulses and/or the reception of echo signals. In the reverse direction, the logics and/or circuits are configured to receive ultrasound echo signals reflected by target tissue and received by the ultrasound transducer elements 324. The logics and/or circuits convert the ultrasound echo signals into electrical signals and transfer the electrical signals through the interposer 330 and the electrical cable 340 to the processing system 130 for processing and/or display. The logics and/or circuits can be further configured to perform signal conditioning before transferring the signals. Signal conditioning may include filtering, amplification, and beamforming. In some embodiments, beamforming can be performed to reduce the number of signal channels. For example, the number of signal channels may be between about 4 to about 128, with some particular embodiments, of about 8. In some embodiments, the IC layer 326 may have a longer length than the acoustic layer 322. The portion 325 of the IC layer 326 extending beyond acoustic layer 322 may include a plating layer 327 for wirebonding to the interposer 330, as described in greater detail herein. The plating layer 327 may be composed of any suitable material such as gold, aluminum, and copper, silver, and ENEPIG.

The backing layer 328 is composed of an acoustically absorptive material so that the backing layer 328 can absorb or deaden the ultrasonic waves coming from the back of the acoustic layer 322. For example, the backing layer 328 may be composed of an epoxy material. In some embodiments, the backing layer 328 may have a longer length than IC layer 326. The portion 329 of the backing layer 328 extending beyond the IC layer 326 may function as an alignment agent for aligning the interposer 330 to the imaging component 320, as described in greater detail herein.

Dimensions of the imaging component 320 may vary in different embodiments and may be limited by the space available in the tip member 310. For example, the acoustic layer 322, the IC layer 326, and the backing layer 328 may have about the same width 408, which may be in the range of about 1 mm to about 4 mm. The acoustic layer 322 may have a length 402 of about 5 mm to about 15 mm. The IC layer 326 may have a length 404 of about 5 mm to about 20 mm. The backing layer 328 may have a length 406 of about 5 mm to about 30 mm.

Figure 5:
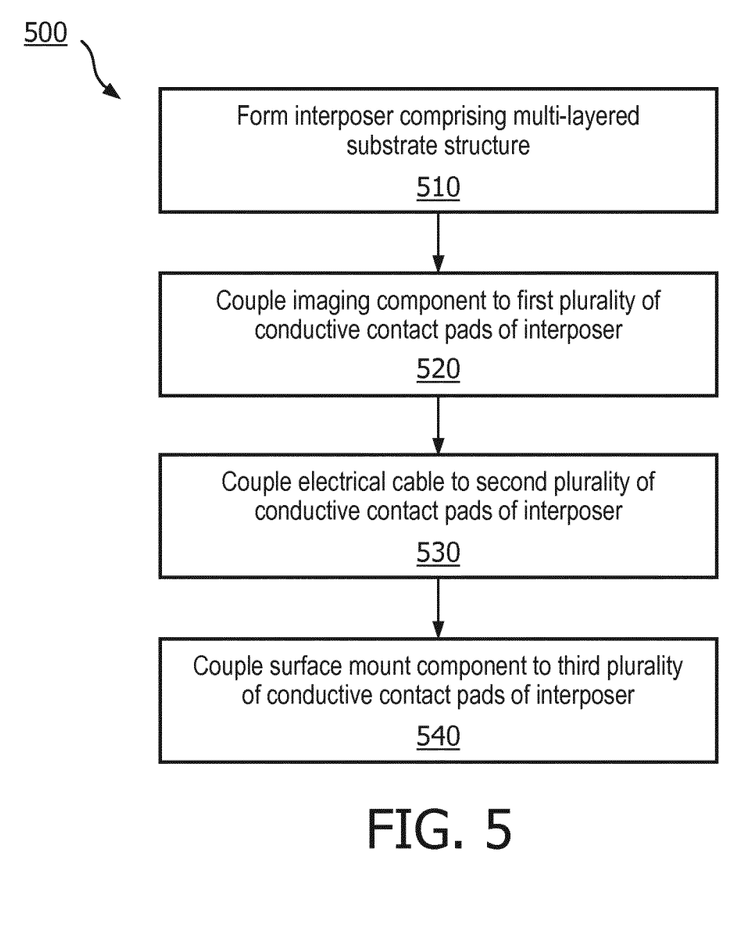
FIG. 5 is a flow diagram of a method of manufacturing a tip assembly according to embodiments of the present disclosure.
Figure 6:
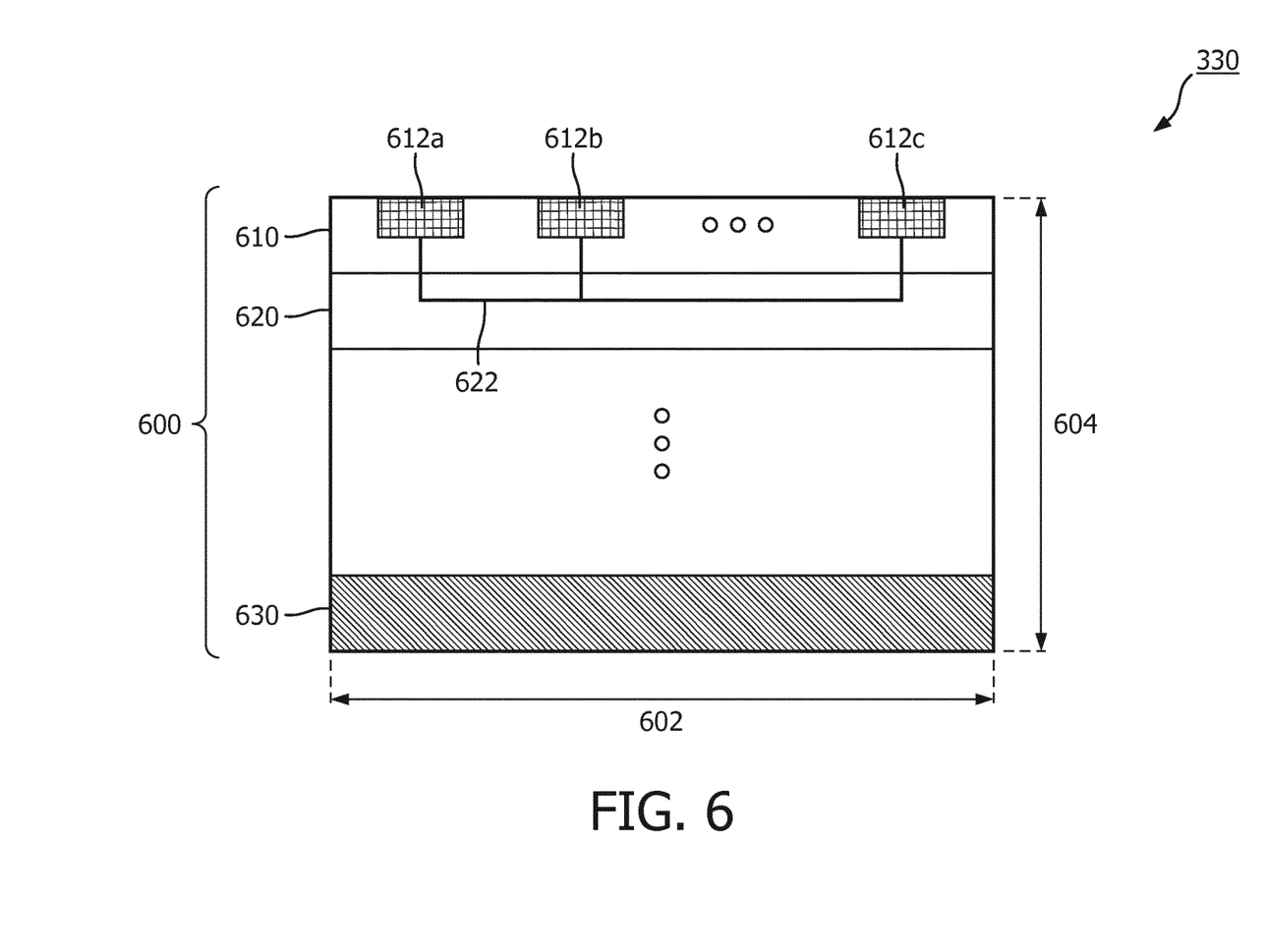
FIG. 6 is a cross-sectional view of an interposer according to embodiments of the present disclosure.
Figure 7:
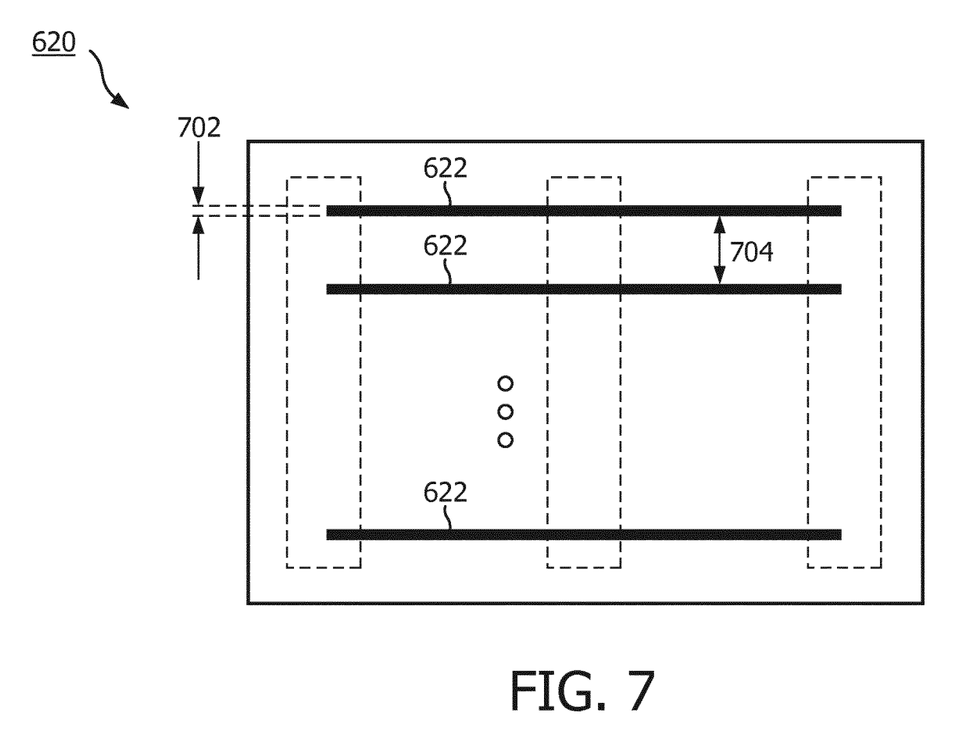
FIG. 7 is a top view of an intermediate conductive layer of an interposer according to embodiments of the present disclosure.
Figure 8:
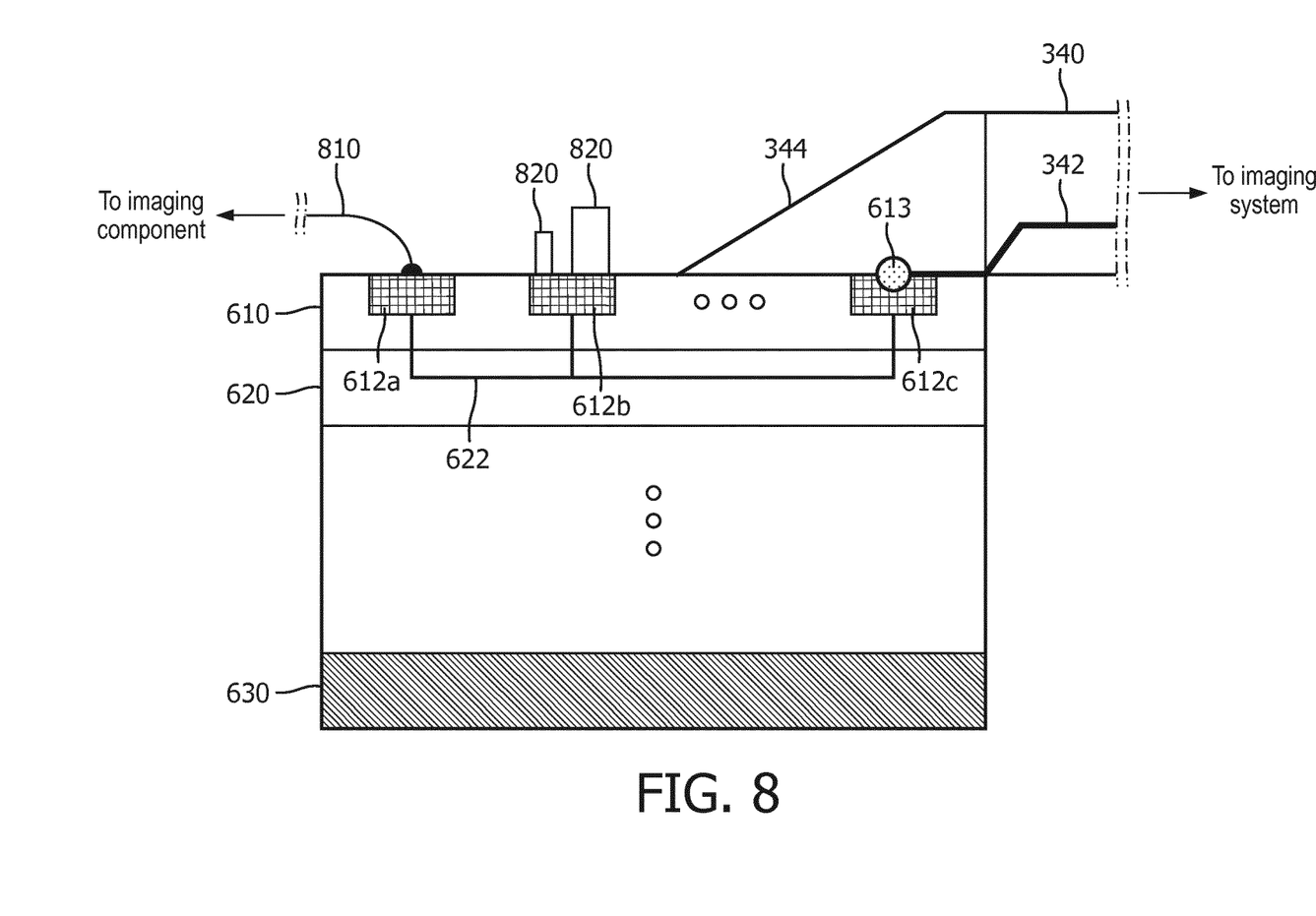
FIG. 8 is a cross-sectional view of an interposer with a bond wire and an electrical cable coupled in position according to embodiments of the present disclosure.
Figure 9:
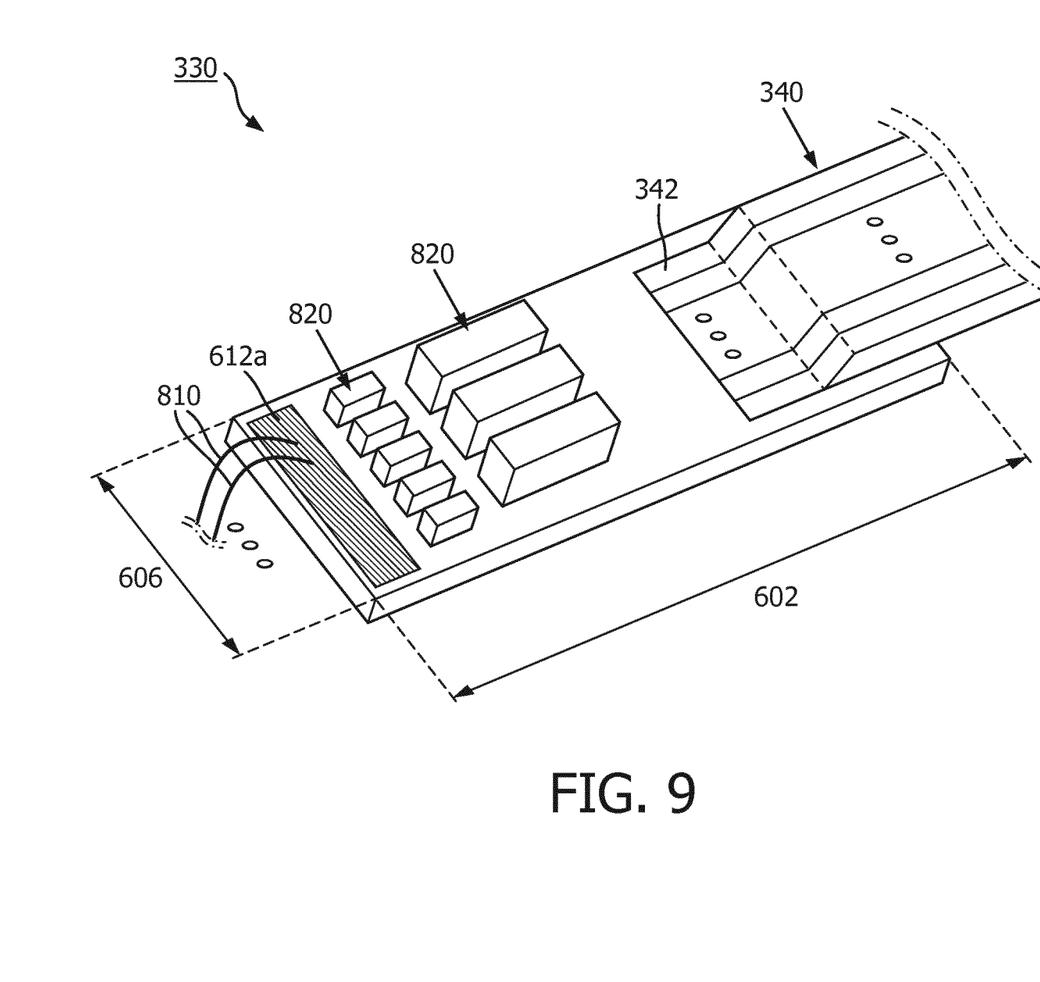
FIG. 9 is a perspective view of an interposer with an electrical cable and surface-mount components coupled in position according to embodiments of the present disclosure.
Figure 10:
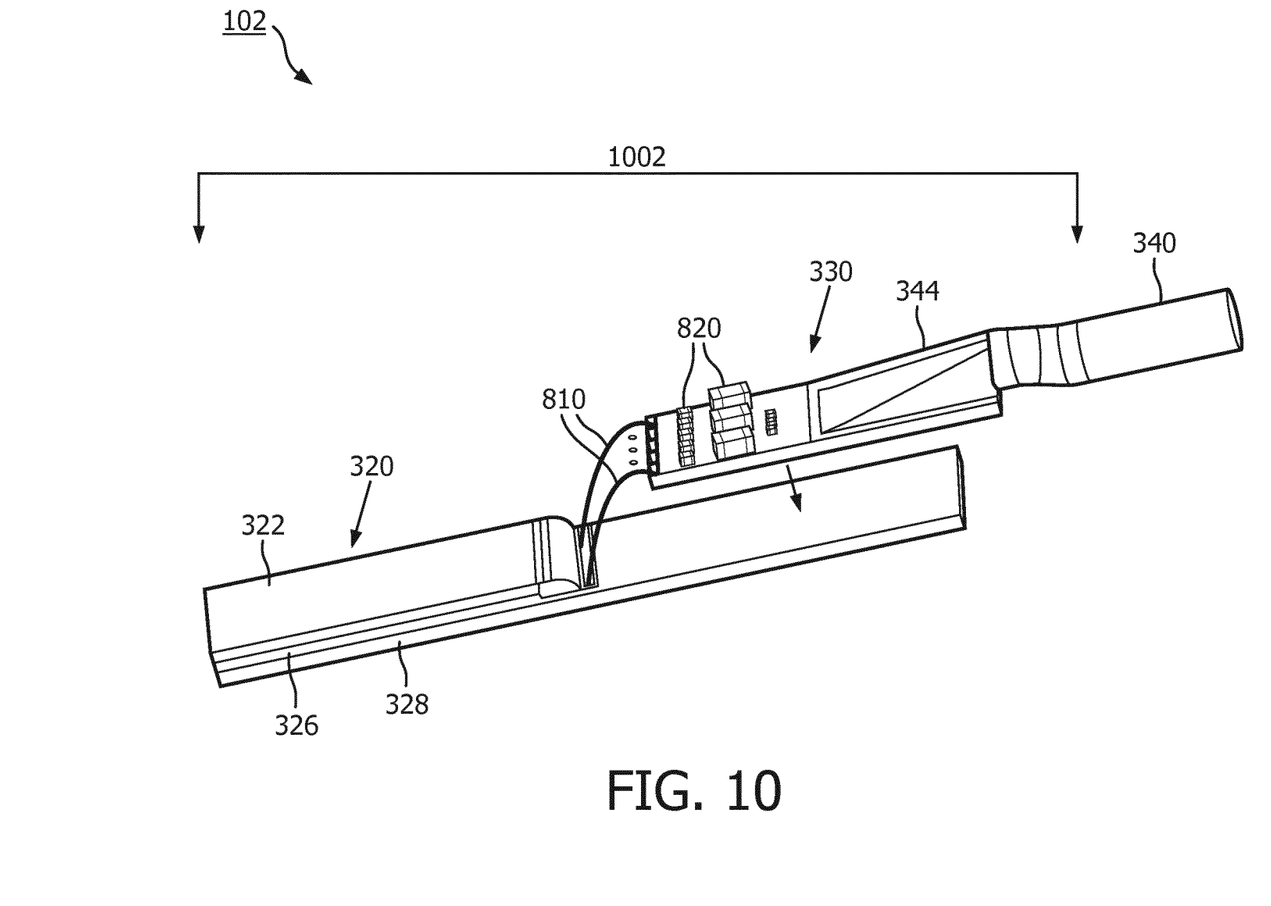
FIG. 10 is a perspective view of an interposer and an imaging component positioned for coupling according to embodiments of the present disclosure.

A method 500 of manufacturing the tip assembly 102 is described with reference made to FIGS. 5-9. FIG. 5 is a flow diagram of a method 500 of manufacturing the tip assembly 102 according to embodiments of the present disclosure. It is understood that additional steps can be provided before, during, and after the steps of method 500, and some of the steps described can be replaced or eliminated for other embodiments of the method. The steps of the method 500 can be carried out by a manufacturer of a catheter in the order as shown or any suitable order. FIG. 6 is a cross-sectional view of the interposer 330 taken along the line 309 of FIG. 3 according to embodiments of the present disclosure. FIG. 7 is a top view of an intermediate conductive layer 620 of the interposer 330 according to embodiments of the present disclosure. FIG. 8 is a cross-sectional view of the interposer 330 taken along the line 309 of FIG. 3 with a bond wire 810 and the electrical cable 340 coupled in position according to embodiments of the present disclosure. FIG. 9 is a perspective view of the interposer 330 with the electrical cable 340 and surface-mount components 820 coupled in position according to embodiments of the present disclosure. FIG. 10 is a perspective of the interposer 330 and the imaging component 320 positioned for coupling according to embodiments of the present disclosure.

Referring to the step 510 of the method 500 and FIGS. 6 and 7, in an embodiment, an interposer comprising a multi-layered substrate structure 600 is formed. The multi-layered substrate structure 600 includes a first plurality of conductive contact pads 612a, a second plurality of conductive contact pads 612b, and a third plurality of conductive contact pads 612c coupled by a plurality of conductive lines 622. FIG. 6 illustrates the multi-layered substrate structure 600. The multi-layered substrate structure 600 includes a top conductive layer 610, one or more intermediate conductive layers 620, and a base layer 630. The intermediate conductive layers 620 are positioned between the top conductive layer 610 and the base layer 630. The base layer 630 can be compose of any suitable substrate material, such as such as ceramic, glass, quartz, alumina, sapphire, and silicon, which may doped or un-doped. In some embodiments, standard semiconductor fabrication processes may be used to form the multi-layered substrate structure 600. When using un-doped silicon for the base layer 630, an additional insulating layer (e.g., SiO2 (silica)) may be disposed between the silicon base layer 630 and the conductive layers 620.

The top conductive layer 610 and the intermediate conductive layers 620 are composed of conductive materials such as aluminum or copper. The top conductive layer 610 is plated to form the conductive contact pads 612 for connecting to the imaging component 320, the electrical cable 340, and/or other components for power regulation. In an embodiment, the conductive contact pads 612 can be composed of or plated with electroless nickel palladium immersion gold (ENEPIG) materials, which are materials are suitable for both soldering and wirebonding.

The intermediate conductive layers 620 are patterned to form the conductive lines 622, for example, using masking and photolithography processes that are commonly used for semiconductor fabrication. The conductive lines 622 form signal paths between the conductive contact pads 612. FIG. 7 illustrates a top view of an exemplary intermediate conductive layer 620. As shown, the conductive lines 622 are patterned on the intermediate conductive layer 620. Although the conductive lines 622 are shown as straight lines, the conductive lines 622 may be patterned in any suitable configuration. The dashed boxes show areas which may be coupled to the conductive contact pads 612 when stacked with the top conductive layer 610. Dimensions of the conductive lines 622 may vary in different embodiments and may be dependent the fabrication process. In some embodiments, the conductive lines 622 can have widths 702 between about 1 μm to about 50 μm and may be spaced apart by a spacing 704 of about 1 μm to about 50 μm.

The conductive lines 622 may extend through one or more of intermediate conductive layers 620. The number of intermediate conductive layers 620 may vary depending on the number of conductive lines 622 and the required resistances for the conductive lines 622. In some embodiments, the multi-layered substrate structure 600 can have about 5 intermediate conductive layers 620. In addition, the multi-layered substrate structure 600 may include dielectric layers between adjacent layers to provide insulation and/or protection to the conductive lines 622.

Dimensions of the multi-layered substrate structure 600 may vary in different embodiments and may be limited by the size of the tip member 310. In some embodiments, the multi-layered substrate structure 600 includes a length 602 of less than about 15 mm, a thickness 604 of less than about 0.5 mm, and a width 606 (shown in FIG. 9) of less than 4 mm.

Referring to the step 520 of the method 500 and FIGS. 8-10, in an embodiment, the imaging component 320 is coupled to the first plurality of conductive contact pads 612a of the interposer 330, for example, using wirebonding technology such as thermal compression wirebonding. As described above, the IC layer 326 of the imaging component 320 may generate a number of signal channels for transferring ultrasound echo signals to the electrical cable 340 for image generation. In an embodiment, the multi-layered substrate structure 600 connects each signal channel output by the IC layer 326 of the imaging component 320 via a bond wire 810. The bond wire 810 may be composed of any suitable materials such as gold, aluminum, or copper. As shown in FIGS. 7-10, one end of each bond wire 810 is bonded to one of the first plurality of conductive contact pads 612a. The opposite end of each bond wire 810 is bonded to the plating layer 327 of the IC layer 326. For example, the plating layer 327 may include a plurality of contact pads coupled to the signal channel outputs.

Referring to the step 530 of the method 500 and FIGS. 8-10, in an embodiment, the electrical cable 340 is coupled to the second plurality of conductive contact pads 612c of the interposer 330, for example, using soldering. As described above, the electrical cable 340 carries the signal channel outputs (e.g., the beamformed or multiplexed ultrasound echo signals) of the IC layer 326 to the processing system 130. As shown in FIGS. 8 and 9, the electrical cable 340 includes a plurality of conductors or conductive elements 342. For example, each signal channel output is carried by one conductive element 342. In addition, one or more of the conductive elements 342 can carry control signals for controlling the ultrasound transducer elements 324. For example, the control signals may be generated by the processing system 130 or other interface modules positioned between the processing system 130 and the intraluminal device 110. Further, one or more of the conductive elements 342 can carry power for powering the imaging component 320. The conductive elements 342 can be soldered to the first plurality of conductive contact pads 612c using any suitable soldering material (e.g., tin, lead, and/or zinc) as shown by the soldering joint 613. As shown in FIG. 10, the electrical cable 340 is coupled to a protector 344 protecting the portions of the conductive elements 342 that are positioned on the surface of the interposer 330.

Referring to the step 540 of the method 500 and FIGS. 8-10, in an embodiment, a surface-mount component 820 is mounted on the third plurality of conductive pads 612c. For example, one or more of the surface-mount component 820 can be mounted onto surfaces of one or more of the third plurality of conductive pads 612c via soldering or conductive epoxy as shown in FIGS. 8-10. Some examples of the surface-mount components 820 may include capacitors and thermistors, resistors, diodes, transistors, inductors. Thus, the interposer 330 may include various surface-mount components to provide additional functionalities such as power regulation. It should be noted that the step 540 may be optional in some embodiments.

Figure 11:
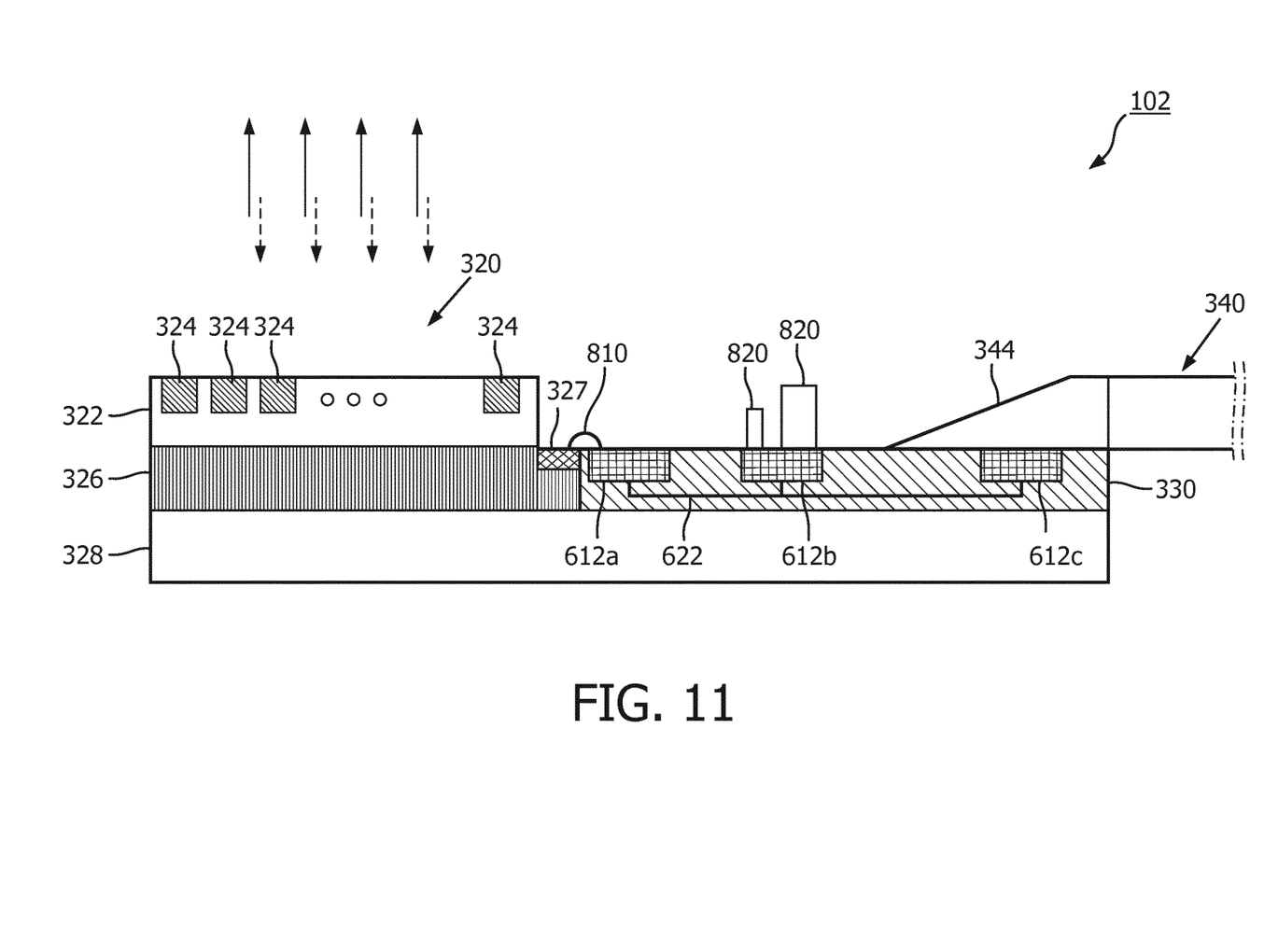
FIG. 11 is a cross-sectional view of an interposer and an imaging component coupled in position according to embodiments of the present disclosure.

FIG. 11 is a cross-sectional view of the interposer 330 and the imaging component 320 coupled in position according to embodiments of the present disclosure. The cross-sectional view is taken along the line 1002 of FIG. 10. The ultrasound transducer elements 324 in the acoustic layer 322 emit ultrasound signals (shown as solid arrows) and receive ultrasound echo signals (shown as dashed arrows) reflected by surrounding vasculatures when in use. The logics and/or circuits of the IC layer 326 convert and process the ultrasound echo signals into electrical signals and transfer the electrical signals to the electrical cable 340 via the bond wires 810, the conductive contact pads 612, and the conductive lines 622 of the interposer 330.

The interposer 330 provides several benefits. The interposer 330 can facilitate stable interconnect between the imaging component 320 and the electrical cable 340. The interposer 330 can form the conductive lines 622 with high density and high precision. As described above, the conductive lines 622 can have widths between about 1 μm to about 50 μm and spaced apart by about 1 μm to about 50 μm, whereas typical PCBs and/or flex circuits have traces with widths between about 25 μm to about 100 μm and spaced apart by about 25 μm to about 100 μm. Thus, the disclosed embodiments can reduce the form factor of the interposer 330 by at least an order of about 10 when compared to PCBs and/or flex circuits. As such, the interposer 330 is suitable for use in a catheter assembly. In addition, the inclusion of the EPENIG conductive contact pads 612 in the top conductive layer 610 allows the interposer 330 to be soldered to the electrical cable 340 and wire-bonded to the imaging component 320. The interposer 330 can include additional functionalities by including surface-mount components soldered to the EPENIG conductive contact pads 612. Further, the interposer 330 can be fabricated in batches. In an embodiment, hundreds of the multi-layered substrate structures 600 can be formed on a wafer with a precise singulation, for example, about 8 µm of clearance from the outermost conductive lines 622 to the edges or cut lines of the interposer 330 part.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An imaging catheter assembly, comprising:
    an interposer including a proximal end, a distal end, and a multi-layered substrate structure, wherein the multi-layered substrate structure includes a first plurality of conductive contact pads coupled to a second plurality of conductive contact pads via a plurality of conductive lines;
    an imaging component coupled to the interposer via the first plurality of conductive contact pads, wherein the imaging component includes an ultrasound transducer array including a proximal end and a distal end, wherein the distal end of the interposer is proximal to the proximal end of the ultrasound transducer array; and
    an electrical cable coupled to the interposer via the second plurality of conductive contact pads and in communication with the imaging component,
    wherein the imaging component includes an integrated circuit (IC) layer positioned between an acoustic layer and a backing layer,
    wherein the backing layer is longer than the IC layer such that a portion of the backing layer extends beyond the IC layer, and
    wherein the interposer is positioned on the portion of the backing layer that extends beyond the IC layer.

2. The imaging catheter assembly of claim 1, wherein the interposer includes:
    a top conductive layer including the first plurality of conductive contact pads and the second plurality of conductive contact pads;
    a base substrate material layer; and
    at least one intermediate conductive layer positioned between the top conductive layer and the base substrate material layer, wherein the plurality of conductive lines extend through the at least one intermediate conductive layer.

3. The imaging catheter assembly of claim 2, wherein the base substrate material layer includes at least one of ceramic, glass, quartz, alumina, sapphire, or silicon.

4. The imaging catheter assembly of claim 2, wherein the top conductive layer further includes:
    a third plurality of conductive contact pads coupled to the plurality of conductive lines; and
    a surface-mount component mounted on the third plurality of conductive contact pads.

5. The imaging catheter assembly of claim 4, wherein the surface-mount component is a power-regulating component.

6. The imaging catheter assembly of claim 1, wherein the interposer has a width less than 4 millimeter.

7. The imaging catheter assembly of claim 1, wherein the interposer has a length less than 15 millimeter.

8. The imaging catheter assembly of claim 1, wherein the imaging component is wire-bonded to the interposer via the first plurality of conductive contact pads.

9. The imaging catheter assembly of claim 8, wherein the electrical cable is soldered to the interposer via the second plurality of conductive contact pads.

10. The imaging catheter assembly of claim 1, wherein the imaging component includes an integrated circuit (IC) layer positioned between an acoustic layer and a backing layer.

11. The imaging catheter assembly of claim 10, wherein the imaging component is a planar component, and wherein the interposer is positioned coplanar or parallel to a plane of the imaging component.

12. The imaging catheter assembly of claim 1, wherein the plurality of conductive lines includes at least one of a power line, a control line, or a signal line.

13. The imaging catheter assembly of claim 1, further comprising a flexible elongate member including a distal portion and a proximal portion, wherein the imaging component and the interposer are coupled to the distal portion of the flexible elongate member.

14. An imaging catheter assembly, comprising:
    an interposer including a proximal end, a distal end, and a multi-layered substrate structure, wherein the multi-layered substrate structure includes a first plurality of conductive contact pads coupled to a second plurality of conductive contact pads via a plurality of conductive lines;
    an imaging component coupled to the interposer via the first plurality of conductive contact pads, wherein the imaging component includes an ultrasound transducer array including a proximal end and a distal end, wherein the distal end of the interposer is proximal to the proximal end of the ultrasound transducer array; and
    an electrical cable coupled to the interposer via the second plurality of conductive contact pads and in communication with the imaging component,
    wherein the imaging component includes a backing layer including a proximal portion and a distal portion, and
    wherein the ultrasound transducer array is positioned over the distal portion of the backing layer and the interposer is positioned over the proximal portion of the backing layer.

15. The imaging catheter assembly of claim 14, wherein the interposer includes:
    a top conductive layer including the first plurality of conductive contact pads and the second plurality of conductive contact pads;
    a base substrate material layer; and
    at least one intermediate conductive layer positioned between the top conductive layer and the base substrate material layer, wherein the plurality of conductive lines extend through the at least one intermediate conductive layer.

16. The imaging catheter assembly of claim 15, wherein the base substrate material layer includes at least one of ceramic, glass, quartz, alumina, sapphire, or silicon.

17. The imaging catheter assembly of claim 15, wherein the top conductive layer further includes:
    a third plurality of conductive contact pads coupled to the plurality of conductive lines; and a surface-mount component mounted on the third plurality of conductive contact pads.

18. The imaging catheter assembly of claim 17, wherein the surface-mount component is a power-regulating component.

19. The imaging catheter assembly of claim 14, wherein the interposer has a width less than 4 millimeter.

20. The imaging catheter assembly of claim 14, wherein the interposer has a length less than 15 millimeter.

21. The imaging catheter assembly of claim 14, wherein the imaging component is wire-bonded to the interposer via the first plurality of conductive contact pads.

22. The imaging catheter assembly of claim 21, wherein the electrical cable is soldered to the interposer via the second plurality of conductive contact pads.

23. The imaging catheter assembly of claim 14, wherein the imaging component includes an integrated circuit (IC) layer positioned between an acoustic layer and the backing layer.

24. The imaging catheter assembly of claim 23, wherein the imaging component is a planar component, and wherein the interposer is positioned coplanar or parallel to a plane of the imaging component.

25. The imaging catheter assembly of claim 14, wherein the plurality of conductive lines includes at least one of a power line, a control line, or a signal line.

26. The imaging catheter assembly of claim 14, further comprising a flexible elongate member including a distal portion and a proximal portion, wherein the imaging component and the interposer are coupled to the distal portion of the flexible elongate member.

* * * * *